United States Patent
Caponigro et al.

(10) Patent No.: US 9,700,557 B2
(45) Date of Patent: Jul. 11, 2017

(54) PHARMACEUTICAL COMBINATIONS OF A CDK4/6 INHIBITOR AND A B-RAF INHIBITOR

(71) Applicant: NOVARTIS AG, Basel (CH)

(72) Inventors: Giordano Caponigro, Foxborough, MA (US); Darrin Stuart, Pleasant Hill, CA (US); Sunkyu Kim, Arlington, MA (US); Alice Loo, Medford, MA (US); Scott Delach, Waltham, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/414,998

(22) PCT Filed: Jul. 25, 2013

(86) PCT No.: PCT/US2013/051990
§ 371 (c)(1),
(2) Date: Jan. 15, 2015

(87) PCT Pub. No.: WO2014/018725
PCT Pub. Date: Jan. 30, 2014

(65) Prior Publication Data
US 2015/0164897 A1    Jun. 18, 2015

Related U.S. Application Data

(60) Provisional application No. 61/676,134, filed on Jul. 26, 2012, provisional application No. 61/830,911, filed on Jun. 4, 2013.

(51) Int. Cl.
*A61K 31/519* (2006.01)
*A61K 31/4184* (2006.01)
*A61K 31/506* (2006.01)

(52) U.S. Cl.
CPC ........ *A61K 31/519* (2013.01); *A61K 31/4184* (2013.01); *A61K 31/506* (2013.01)

(58) Field of Classification Search
CPC . A61K 31/519; A61K 31/506; A61K 31/4184
(Continued)

(56) References Cited

U.S. PATENT DOCUMENTS

2004/0116710 A1*   6/2004  Wallace ............... C04B 35/632
                                                      548/113

FOREIGN PATENT DOCUMENTS

CN          1874768 A      12/2006
CN        102186856 A       9/2011
(Continued)

OTHER PUBLICATIONS

E. Huillard et al.: "Cooperative interactions of BRAFV600E kinase and CDKN2A locus deficiency in pediatric malignant astrocytoma as a basis for rational therapy", Proceedings of the National Academy of Sciences, vol. 109, No. 22, pp. 8710-8715, 2012.
(Continued)

*Primary Examiner* — San-Ming Hui
(74) *Attorney, Agent, or Firm* — Brian C. Trinque; Lathrop & Gage LLP

(57) ABSTRACT

A pharmaceutical combination comprising (a) CDK4/6 inhibitor (b) a B-Raf inhibitor, and optionally (c) a MEK 1/2 inhibitor; combined preparations and pharmaceutical compositions thereof; the uses of such combination in the treatment of proliferative diseases; and methods of treating a subject suffering from a proliferative disease comprising administering a therapeutically effective amount of such combination.

13 Claims, 1 Drawing Sheet

(58) Field of Classification Search
USPC .................................. 514/265.1, 275, 367
See application file for complete search history.

(56) References Cited

FOREIGN PATENT DOCUMENTS

| WO | 2005023251 A1 | | 3/2005 |
|---|---|---|---|
| WO | 2005/094830 | | 10/2005 |
| WO | 2010/006225 A1 | | 1/2010 |
| WO | 2010020675 A1 | | 2/2010 |
| WO | WO2010020675 | * | 2/2010 |
| WO | 2011025927 A1 | | 3/2011 |
| WO | WO2011025927 | * | 3/2011 |
| WO | 2011/130232 A1 | | 10/2011 |

OTHER PUBLICATIONS

Zhao Y et al.: "Simultaneous knockdown of BRAF and expression of INK4A in melanoma cells leads to potent growth inhibition and apoptosis", Biochemical and Biophysical Research Communications, vol. 370, No. 3, pp. 509-513, 2008.

T.C. Tortelli et al.: "Abstract 5598: Interaction between BRAF inhibitor PLX-4720 and CDK inhibitors can sensitize melanoma cells with BRAF V600E mutation", Cancer Research, vol. 72, No. 8, Suppl 15, pp. 5598-5598, 2012.

Li Jing et al.: "Simultaneous inhibition of MEK and CDK leads to potent apoptosis in human melanoma cells", Cancer Investigation, vol. 28, No. 4, pp. 350-356, 2010.

Paolo A Ascierto et al.: "The role of BRAF V600 mutation in melanoma", Journal of Translational Medicine, vol. 10, No. 1, p. 85, 2012.

Inamdar G S et al.: "Targeting the MAPK pathway in melanoma: Why some approaches succeed and other fail", Biochemical Pharmacology, vol. 80, No. 5, pp. 624-637, 2010.

Lackner et al. (2010) "Prospects for personalized medicine with inhibitors targeting the RAS and PI3K pathways," Expert Rev. Mol. Diag. 10(1):75-87.

* cited by examiner

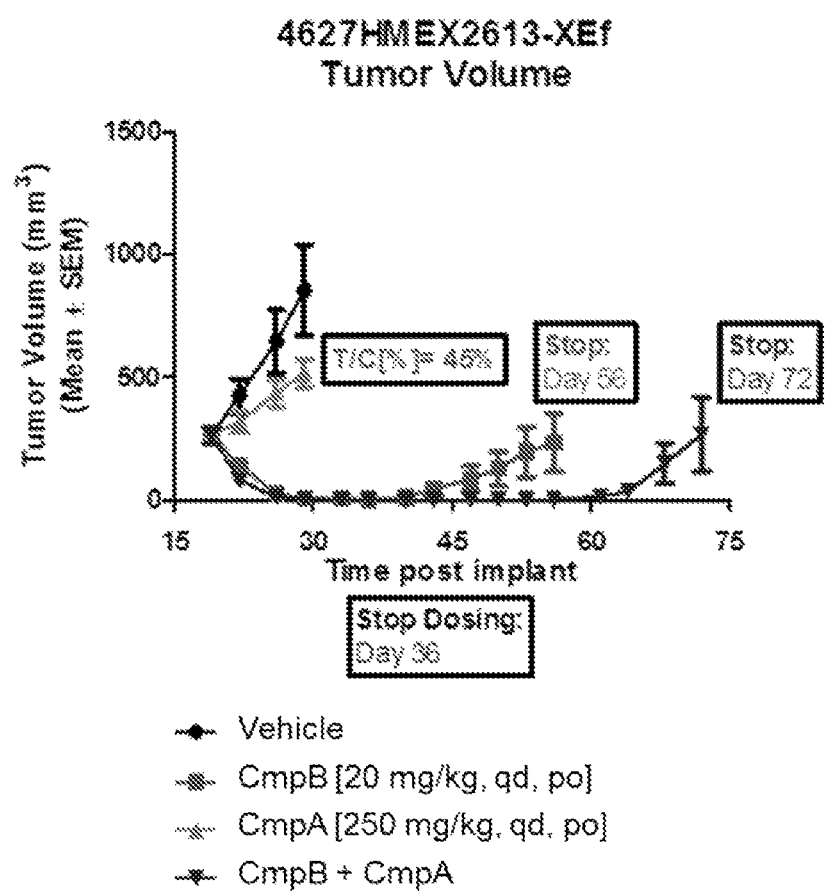

PHARMACEUTICAL COMBINATIONS OF A CDK4/6 INHIBITOR AND A B-RAF INHIBITOR

FIELD OF THE INVENTION

A combination of a cyclin dependent kinase 4/6 (CDK4/6) inhibitor, a B-Raf kinase inhibitor and optionally a Mitogen-activated protein kinase kinase (MEK 1/2 or MEK) inhibitor which is used for the treatment of proliferative diseases. This invention also relates to the uses of such a combination in the treatment of proliferative diseases; to pharmaceutical compositions of the combination of agents and methods of treating a subject suffering from a proliferative disease comprising administering a therapeutically effective amount of such a combination to the subject.

BACKGROUND OF THE INVENTION

Tumor development is closely associated with genetic alteration and deregulation of cyclin dependent kinases (CDKs) and their regulators, suggesting that inhibitors of CDKs may be useful anti-cancer therapeutics. The function of CDKs is to phosphorylate and thus activate or deactivate certain proteins. The catalytic step mediated by CDKs involves a phospho-transfer reaction from ATP to the macromolecular enzyme substrate. Several groups of compounds (reviewed in e.g. Fischer, P. M. Curr. Opin. Drug Discovery Dev. 2001, 4, 623-634) have been found to possess anti-proliferative properties by virtue of CDK-specific ATP antagonism.

At a molecular level mediation of CDK/cyclin complex activity requires a series of stimulatory and inhibitory phosphorylation, or dephosphorylation, events. CDK phosphorylation is performed by a group of CDK activating kinases (CAKs) and/or kinases such as wee1, Myt1 and Mik1. Dephosphorylation is performed by phosphatases such as cdc25(a & c), pp2a, or KAP.

CDK/cyclin complex activity may be further regulated by two families of endogenous cellular proteinaceous inhibitors: the Kip/Cip family, or the INK family. The INK proteins specifically bind CDK4 and CDK6. p16ink4 (also known as MTS1) is a potential tumour suppressor gene that is mutated or deleted in a large number of primary cancers. The Kip/Cip family contains proteins such as p21Cip1, Waf1, p27Kip1 and p57kip2, where p21 is induced by p53 and is able to inactivate the CDK2/cyclin(E/A) complex. Atypically low levels of p27 expression have been observed in breast, colon and prostate cancers. Conversely over expression of cyclin E in solid tumours has been shown to correlate with poor patient prognosis. Over expression of cyclin D1 has been associated with oesophageal, breast, squamous, and non-small cell lung carcinomas.

The pivotal roles of CDKs, and their associated proteins, in coordinating and driving the cell cycle in proliferating cells have been outlined above. Some of the biochemical pathways in which CDKs play a key role have also been described. The development of monotherapies for the treatment of proliferative disorders, such as cancers, using therapeutics targeted generically at CDKs, or at specific CDKs, is therefore potentially highly desirable. Thus, there is a continued need to find new therapeutic agents to treat human diseases. The CDK4/6 inhibitors useful in the present combinations are generally and specifically described in published PCT patent application WO2010/020675, which is hereby incorporated by reference.

The protein kinases represent a large family of proteins, which play a central role in the regulation of a wide variety of cellular processes and maintaining control over cellular function. Aberrant kinase activity has been observed in many disease states including benign and malignant proliferative disorders as well as diseases resulting from inappropriate activation of the immune and nervous systems.

The Ras-Raf-MEK-ERK signaling pathway transmits signals from cell surface receptors to the nucleus and is essential for cell proliferation and survival. Since 10-20% of human cancers harbor oncogenic Ras mutation and many human cancers have activated growth factor receptors, this pathway is an ideal target for intervention.

The Raf family of serine/threonine kinases include three members: C-Raf (or Raf-1), B-Raf and A-Raf. Activating alleles of B-Raf have been identified in ~70% of melanomas, 40% of papillary thyroid carcinoma, 30% of ovarian low-grade carcinoma, and 10% of colorectal cancers. Most B-Raf mutations are found within the kinase domain, with a single substitution (V600E) accounting for 80%. The mutated B-Raf proteins activate Raf-MEK-ERK pathway either via elevated kinase activity toward MEK or via activating C-Raf. The B-Raf inhibitor in the present combination therapy inhibits cellular processes involving B-Raf kinase by blocking the signal cascade in these cancer cells and ultimately inducing stasis and/or death of the cells. B-Raf inhibitors useful in the present combinations are generally and specifically described in published PCT patent application WO2011/025927, which is hereby incorporated by reference.

MEK is also a major protein in the RAS/RAF/MEK/ERK pathway, which signals toward cell proliferation and survival, and frequently is activated in tumors that have mutations in the RAS or RAF oncogenes or in growth receptor tyrosine kinases. Despite being only rarely mutated in cancer, inhibitors of the MEK1 and MEK2 proteins have also been targeted for small molecule inhibition owing to their central position within the RAS/RAF/MEK signal transduction pathway signaling cascade.

Appropriate optional MEK 1/2 inhibitors for use in the present combinations are known in the art. MEK 1/2 inhibitors useful in the present invention include PD325901, PD-181461, ARRY142886/AZD6244, ARRY-509, XL518, JTP-74057, AS-701255, AS-701173, AZD8330, ARRY162, ARRY300, RDEA436, E6201, RO4987655/R-7167, GSK1120212 or AS703026.

In an important embodiment, the MEK 1/2 inhibitors include compounds described in WO03/077914, which is here incorporated by reference in its entirety, in particular a compound of formula (II) or (III).

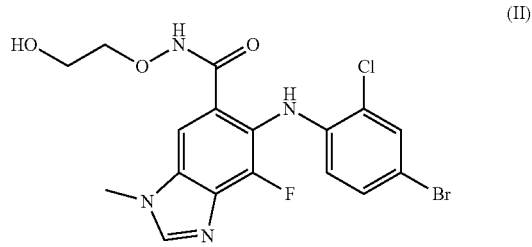

(II)

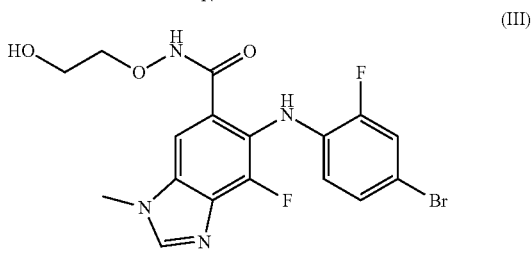

(III)

or pharmaceutically acceptable salts thereof, (hereinafter referred to as Compounds C and D, respectively) and the compounds described in WO05/051906, WO05/023251, WO03/077855, US20050049419, and U.S. Pat. No. 7,235,537, which are here incorporated by reference in their entirety, covering N3-alkylated benzimidazoles and other similar heterocyclic derivatives as MEK 1/2 inhibitors for the treatment of proliferative diseases.

SUMMARY OF THE INVENTION

The present invention relates to a therapeutic combination comprising: (a) a CDK4/6 inhibitor and a B-Raf inhibitor, useful for separate, simultaneous or sequential administration to a subject in need thereof for treating or preventing a proliferative disease.

The present invention especially relates to a therapeutic combination comprising:

(a) a CDK4/6 inhibitor of the formula

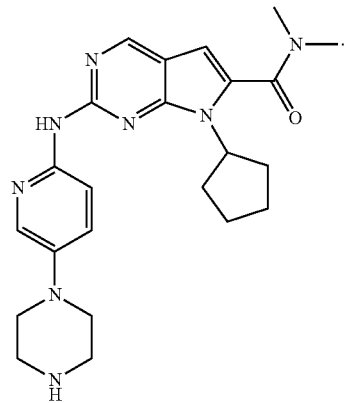 [SMILES: CN(C)C(=O)c1cc2cnc(Nc3ccc(N4CCNCC4)cn3)nc2n1C1CCCC1]

or a pharmaceutically acceptable salt thereof (hereinafter referred to as Compound A), (b) a B-Raf inhibitor of the formula

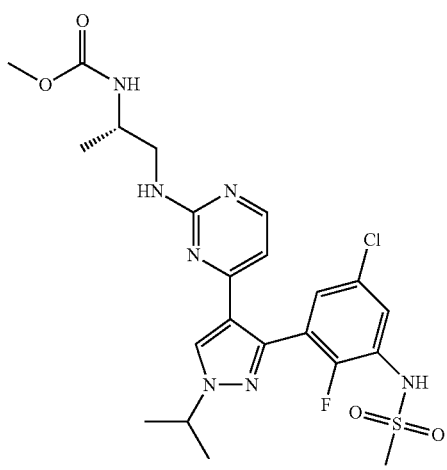

or a pharmaceutically acceptable salt thereof (hereinafter referred to as Compound B), and (c) optionally a MEK 1/2 inhibitor.

Hereinafter, combinations of Compound A and Compound B and the triple combination of Compound A, Compound B and a MEK 1/2 inhibitor will be referred to as a COMBINATION OF THE INVENTION.

The present invention particularly pertains to a COMBINATION OF THE INVENTION useful for separate, simultaneous or sequential administration to a subject in need thereof for treating or preventing a proliferative disease.

The present invention also pertains to a COMBINATION OF THE INVENTION for use in the preparation of a pharmaceutical composition or medicament for the treatment or prevention of a proliferative disease in a subject in need thereof.

The present invention further pertains to the use of a COMBINATION OF THE INVENTION for the preparation of a pharmaceutical composition or medicament for the treatment or prevention of a proliferative disease.

The present invention relates to a method of treating a subject having a proliferative disease comprising administering to said subject a COMBINATION OF THE INVENTION in a quantity which is jointly therapeutically effective against a proliferative disease.

The present invention further provides a commercial package comprising as therapeutic agents a COMBINATION OF THE INVENTION, together with instructions for simultaneous, separate or sequential administration thereof for use in the delay of progression or treatment of a proliferative disease.

BRIEF DESCRIPTION OF THE DRAWINGS

The FIGURE is a graphical representation of the results obtained from Example 2 demonstrating increased durability of response for the COMBINATION OF THE INVENTION.

DETAILED DESCRIPTION OF THE INVENTION

The present invention relates to a therapeutic combination comprising:

(a) a CDK4/6 inhibitor of the formula

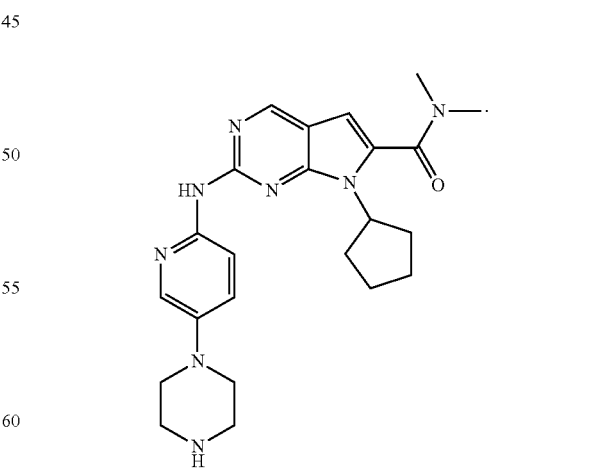

or a pharmaceutically acceptable salt thereof, and (b) a B-Raf inhibitor of the formula

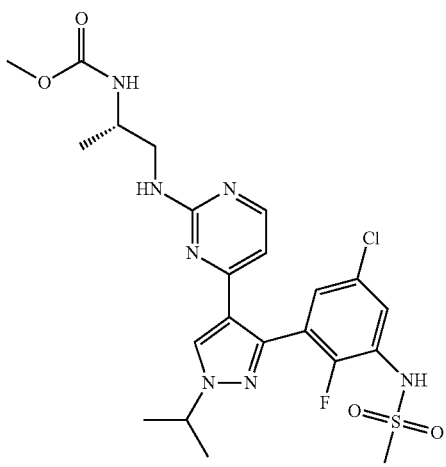 [SMILES: COC(=O)N[C@@H](C)CNc1nccc(-c2cn(C(C)C)nc2-c2cc(Cl)cc(NS(C)(=O)=O)c2F)n1]

or a pharmaceutically acceptable salt thereof, for simultaneous, separate or sequential administration.

The present invention further relates to a pharmaceutical triple combination which further comprises a MEK 1/2 inhibitor.

Thus, the present invention further relates to a therapeutic combination comprising:
(a) a CDK4/6 inhibitor of the formula

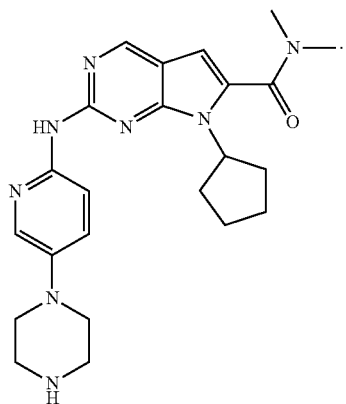 [SMILES: CN(C)C(=O)c1cc2cnc(Nc3ccc(N4CCNCC4)cn3)nc2n1C1CCCC1]

or a pharmaceutically acceptable salt thereof,
(b) a B-Raf inhibitor of the formula

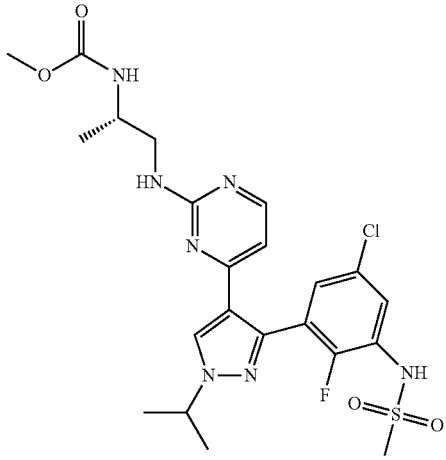 [SMILES: COC(=O)N[C@@H](C)CNc1nccc(-c2cn(C(C)C)nc2-c2cc(Cl)cc(NS(C)(=O)=O)c2F)n1]

or a pharmaceutically acceptable salt thereof, and
(c) a MEK 1/2 inhibitor, for simultaneous, separate or sequential administration.

In an important embodiment of this aspect of the invention, the MEK 1/2 inhibitor is Compound C or Compound D, particularly Compound D, or pharmaceutically acceptable salts thereof.

The COMBINATION OF THE INVENTION is, in particular, for use in the treatment or prevention of a proliferative disease.

The general terms used herein are defined with the following meanings, unless explicitly stated otherwise:

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "combination", "therapeutic combination" or "pharmaceutical combination", as used herein, defines either a fixed combination in one dosage unit form or a kit of parts for the combined administration where Compound A and Compound B (and optionally a MEK 1/2 inhibitor) may be administered independently at the same time or separately within time intervals that allow that the combination partners show a cooperative, e.g., synergistic, effect.

The term "pharmaceutical composition" is defined herein to refer to a mixture or solution containing at least one therapeutic agent to be administered to a subject, e.g., a mammal or human, in order to prevent or treat a particular disease or condition affecting the mammal.

The term "pharmaceutically acceptable" is defined herein to refer to those compounds, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

The term "a combined preparation" is defined herein to refer to especially a "kit of parts" in the sense that the combination partners (a) and (b) and optionally (c), as defined above, can be dosed independently or by use of different fixed combinations with distinguished amounts of the combination partners, i.e., simultaneously or at different time points. The parts of the kit of parts can then e.g., be administered simultaneously or chronologically staggered, that is at different time points and with equal or different time intervals for any part of the kit of parts. The ratio of the total amounts of the combination partner (a) to the combination partner (b) (and if applicable to the combination partner (c)) to be administered in the combined preparation can be varied, e.g., in order to cope with the needs of a patient sub-population to be treated or the needs of the single patient.

The term "co-administration" or "combined administration" as used herein is defined to encompass the administration of the selected therapeutic agents to a single patient, and are intended to include treatment regimens in which the agents are not necessarily administered by the same route of administration or at the same time.

The term "treating" or "treatment" as used herein comprises a treatment relieving, reducing or alleviating at least one symptom in a subject or affecting a delay of progression of a disease. For example, treatment can be the diminishment of one or several symptoms of a disorder or complete eradication of a disorder, such as cancer. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent, delay or treat, or all, as appropriate, development or continuance or aggravation of a disease in a subject.

The term "jointly therapeutically active" or "joint therapeutic effect" means that the therapeutic agents may be given separately (in a chronologically staggered manner, especially a sequence-specific manner) in such time intervals that they prefer, in the warm-blooded animal, especially human, to be treated, still show a (preferably synergistic) interaction (joint therapeutic effect). Whether this is the case can, inter alia, be determined by following the blood levels, showing that both compounds are present in the blood of the human to be treated at least during certain time intervals.

The term "pharmaceutically effective amount" or "clinically effective amount" or "therapeutically effective amount" of a combination of therapeutic agents is an amount sufficient to provide an observable improvement over the baseline clinically observable signs and symptoms of the disorder treated with the combination.

The term "subject" or "patient" as used herein includes animals, which are capable of suffering from or afflicted with a cancer or any disorder involving, directly or indirectly, a cancer. Examples of subjects include mammals, e.g., humans, dogs, cows, horses, pigs, sheep, goats, cats, mice, rabbits rats and transgenic non-human animals. In the preferred embodiment, the subject is a human, e.g., a human suffering from, at risk of suffering from, or potentially capable of suffering from cancers.

The term about" or "approximately" shall have the meaning of within 10%, more preferably within 5%, of a given value or range.

Compound A and/or Compound B and/or the optional MEK 1/2 inhibitor may be administered in free form or in pharmaceutically acceptable salt form.

A "pharmaceutically acceptable salt", as used herein, unless otherwise indicated, includes salts of acidic and basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmaceutically acceptable anions, such as the acetate, benzoate, bromide, chloride, citrate, fumarate, hydrobromide, hydrochloride, iodide, lactate, maleate, mandelate, nitrate, oxalate, salicylate, succinate, and tartrate salts.

Unless otherwise specified, or clearly indicated by the text, reference to therapeutic agents useful in the COMBINATION OF THE INVENTION includes both the free base of the compounds, and all pharmaceutically acceptable salts of the compounds.

The present invention also pertains to a combination such as a combined preparation or a pharmaceutical composition which comprises (a) Compound A and (b) Compound B and optionally Compound D.

The present invention particularly pertains to a COMBINATION OF THE INVENTION useful for treating or preventing a proliferative disease in a subject in need thereof. In this embodiment of the present invention, the COMBINATION OF THE INVENTION is used for the treatment of a proliferative disease comprising administering to the subject a combination therapy, comprising an effective amount of a CDK 4/6 inhibitor selected from COMPOUND A and an effective amount of a B-Raf inhibitor selected from Compound B and optionally an effective amount of a MEK 1/2 inhibitor, especially a MEK 1/2 inhibitor selected from Compound D. Preferably, these inhibitors are administered at therapeutically effective dosages which, when combined, provide a beneficial effect. The administration may be separate, simultaneous or sequential.

In one embodiment, the proliferative disease is cancer. The term "cancer" is used herein to mean a broad spectrum of tumors, including all solid tumors and hematological malignancies. Examples of such tumors include but are not limited to benign or malignant tumors of the brain, lung (in particular small-cell lung cancer and non-small cell lung cancer), squamous cell, bladder, gastric, pancreatic, breast, head and neck, renal, kidney, ureter, ovarian, prostate, colorectal, esophageal, testicular, gynecological (e.g., uterine sarcomas, carcinoma of the fallopian tubes, endometrial, cervix, vagina or vulva), thyroid, pancreatic, bone, skin, melanoma, uterine, ovarian, rectal, anal, colon, testicular, Hodgkin's disease, esophageal, small intestine, endocrine system (e.g., thyroid, parathyroid, or adrenal glands), sarcomas of soft tissues, urethra, penis, leukemia, lymphomas, neoplasms of the central nervous system, sarcomas, myeloma, biliary, liver, neurofibromatosis, acute myelogenous leukemia (AML), myelodysplastic syndromes (MDS), and Kaposi's sarcoma.

In a further embodiment of the present invention, the proliferative disease is melanoma, lung cancer (including non-small cell lung cancer (NSCLC)), colorectal cancer (CRC), breast cancer, kidney cancer such as e.g., renal cell carcinoma (RCC), liver cancer, endometrial cancer, acute myelogenous leukemia (AML), myelodysplastic syndromes (MDS), thyroid cancer, particularly papillary thyroid cancer, pancreatic cancer, neurofibromatosis or hepatocellular carcinoma.

In a further embodiment of the present invention, the proliferative disease is a solid tumor. The term "solid tumor" especially means melanoma, breast cancer, ovarian cancer, colorectal cancer, and generally gastrointestinal tract, cervix cancer, lung cancer (including small-cell lung cancer and non-small cell lung cancer), head and neck cancer, bladder cancer, prostate cancer or Kaposi's sarcoma. The present combination inhibits the growth of solid tumors and also liquid tumors. Further, depending on the tumor type and particular combination used, a decrease of the tumor volume can be obtained. The COMBINATION OF THE INVENTION disclosed herein is also suited to prevent the metastatic spread of tumors and the growth or development of micrometastases. The COMBINATION OF THE INVENTION disclosed herein is suitable for the treatment of poor prognosis patients, especially such poor prognosis patients having metastatic melanoma, colorectal or pancreatic cancer.

In a further embodiment, the proliferative disease is melanoma or colorectal cancer.

The COMBINATION OF THE INVENTION is particularly useful for the treatment of cancers having a genetic alteration in the RAS/RAF/MEK signal transduction pathway such as, for example, a B-Raf mutation or gene amplification.

In an important embodiment, the cancer to be treated is characterized by a B-Raf mutation, e.g., B-Raf mutated colorectal cancer and B-Raf mutated melanoma. In particular, the B-Raf mutation is a V600 mutation, for example a V600E, V600K or V600G mutation.

The nature of proliferative diseases is multifactorial. Under certain circumstances, drugs with different mechanisms of action may be combined. However, just considering any combination of therapeutic agents having different mode of action does not necessarily lead to combinations with advantageous effects.

The administration of a pharmaceutical COMBINATION OF THE INVENTION may result not only in a beneficial effect, e.g. a synergistic therapeutic effect, e.g. with regard to alleviating, delaying progression of or inhibiting the symptoms, but also in further surprising beneficial effects, e.g. fewer side-effects, more durable response, an improved quality of life or a decreased morbidity, compared with a monotherapy applying only one of the pharmaceutically therapeutic agents used in the combination of the invention.

A further benefit is that lower doses of the therapeutic agents of the COMBINATION OF THE INVENTION can be used, for example, such that the dosages may not only often be smaller, but are also may be applied less frequently, or can be used in order to diminish the incidence of side-effects observed with one of the combination partners alone. This is in accordance with the desires and requirements of the patients to be treated.

It can be shown by established test models that a COMBINATION OF THE INVENTION results in the beneficial effects described herein before. The person skilled in the art is fully enabled to select a relevant test model to prove such beneficial effects. The pharmacological activity of a COMBINATION OF THE INVENTION may, for example, be demonstrated in a clinical study or in an animal model as essentially described hereinafter.

Determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients may render impractical the use of this form of testing as a primary model for synergy. However, the observation of synergy in one species can be predictive of the effect in other species and animal models exist, as described herein, to measure a synergistic effect and the results of such studies can also be used to predict effective dose ratio ranges and the absolute doses and plasma concentrations required in other species by the application of pharmacokinetic/pharmacodynamic methods. Established correlations between tumor models and effects seen in man suggest that synergy in animals may be demonstrated by xenograft models.

In one aspect, the present invention provides a synergistic combination for human administration comprising (a) Compound A and (b) Compound B, in a combination range (w/w) which corresponds to the ranges observed in a tumor model. Suitably, the ratio range in humans corresponds to a non-human range selected from between 50:1 to 1:50 parts by weight.

According to a further aspect, the present invention provides a synergistic combination for administration to humans comprising Compound A and Compound B, where the dose range of each component corresponds to the synergistic ranges suggested in a suitable tumor model or clinical study. In general, compound A is administered in a dose in the range from 10 mg to 2000 mg per day, and compound B is administered in a dose in the range from 10 mg to 1000 mg per day, for example 50 mg to 600 mg per day.

In the COMBINATION OF THE INVENTION, Compound A is preferably administered at a dose of 100 to 900 mg/day, preferably 200 to 900 mg/day, for example, 200, 400, 700 or 900 mg/day; Compound B is preferably administered at a dose of 150 to 600 per day, preferably 400 to 600 per day, particularly 450 or 600 mg/day; and, as the optional MEK 1/2 inhibitor, Compound D is administered at a dose of 15 to 150 mg/day, preferably administered on a BID schedule, for example, 15 to 60 mg BID, for example, 45 mg BID.

It is one objective of this invention to provide a pharmaceutical composition, comprising the COMBINATION OF THE INVENTION which is jointly therapeutically effective against a proliferative disease. In this composition, the combination partners can be administered in a single formulation or unit dosage form, administered concurrently but separately, or administered sequentially by any suitable route. The unit dosage form may also be a fixed combination.

The pharmaceutical compositions for separate administration of the combination partners, or for the administration in a fixed combination, i.e. a single galenical composition comprising the COMBINATION OF THE INVENTION, may be prepared in a manner known per se and are those suitable for enteral, such as oral or rectal, and parenteral administration to mammals (warm-blooded animals), including humans, comprising a therapeutically effective amount of at least one pharmacologically active combination partner alone, e.g. as indicated above, or in combination with one or more pharmaceutically acceptable carriers, especially suitable for enteral or parenteral application.

The novel pharmaceutical composition contains may contain, from about 0.1% to about 99.9%, preferably from about 1% to about 60%, of the therapeutic agent(s).

Suitable pharmaceutical compositions for the combination therapy for enteral or parenteral administration are, for example, those in unit dosage forms, such as sugar-coated tablets, tablets, capsules or suppositories, or ampoules. If not indicated otherwise, these are prepared in a manner known per se, for example by means of various conventional mixing, comminution, direct compression, granulating, sugar-coating, dissolving, lyophilizing processes, melt granulation, or fabrication techniques readily apparent to those skilled in the art. It will be appreciated that the unit content of a combination partner contained in an individual dose of each dosage form need not in itself constitute an effective amount since the necessary effective amount may be reached by administration of a plurality of dosage units.

In one embodiment, the present invention also pertains to a COMBINATION OF THE INVENTION for use in the preparation of a pharmaceutical composition or medicament for the treatment or prevention of a proliferative disease in a subject in need thereof.

In accordance with the present invention, a therapeutically effective amount of each of the combination partner of the COMBINATION OF THE INVENTION may be administered simultaneously or sequentially and in any order, and the components may be administered separately or as a fixed combination. For example, the method of treating a proliferative disease according to the invention may comprise (i) administration of the agent (a) in free or pharmaceutically acceptable salt form and (ii) administration of agent (b) in free or pharmaceutically acceptable salt form, (and optionally agent (c) in free or pharmaceutically acceptable salt form, simultaneously or sequentially in any order, in jointly therapeutically effective amounts, preferably in synergistically effective amounts, e.g. in daily or intermittently dosages corresponding to the amounts described herein. The individual combination partners of the COMBINATION OF THE INVENTION may be administered separately at different times during the course of therapy or concurrently in divided or single combination forms. The invention is therefore to be understood as embracing all such regimens of simultaneous or alternating treatment and the term "administering" is to be interpreted accordingly.

The effective dosage of each of the combination partners employed in the COMBINATION OF THE INVENTION may vary depending on the particular compound or pharmaceutical composition employed, the mode of administration, the condition being treated, and the severity of the condition being treated. Thus, the dosage regimen of the COMBINATION OF THE INVENTION is selected in accordance with a variety of factors including the route of administration and the renal and hepatic function of the patient.

The optimum ratios, individual and combined dosages, and concentrations of the combination partners (a) and (b) of the COMBINATION OF THE INVENTION that yield efficacy without toxicity are based on the kinetics of the therapeutic agents' availability to target sites, and are determined using methods known to those of skill in the art.

The effective dosage of each of the combination partners may require more frequent administration of one of the compound(s) as compared to the other compound(s) in the combination. Therefore, to permit appropriate dosing, packaged pharmaceutical products may contain one or more dosage forms that contain the combination of compounds, and one or more dosage forms that contain one of the combination of compounds, but not the other compound(s) of the combination.

When the combination partners, which are employed in the COMBINATION OF THE INVENTION, are applied in the form as marketed as single drugs, their dosage and mode of administration can be in accordance with the information provided on the package insert of the respective marketed drug, if not mentioned herein otherwise.

The optimal dosage of each combination partner for treatment of a proliferative disease can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages may be established using routine testing and procedures that are well known in the art.

The amount of each combination partner that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

Frequency of dosage may vary depending on the compound used and the particular condition to be treated or prevented. Patients may generally be monitored for therapeutic effectiveness using assays suitable for the condition being treated or prevented, which will be familiar to those of ordinary skill in the art.

The present invention relates to a method of treating a subject having a proliferative disease comprising administered to said subject a COMBINATION OF THE INVENTION in a quantity, which is jointly therapeutically effective against a proliferative disease. In particular, the proliferative disease to be treated with a COMBINATION OF THE INVENTION is a melanoma or colorectal cancer, particularly a B-Raf mutated melanoma or colorectal cancer, for example, a V600 B-Raf mutated melanoma or colorectal cancer. Furthermore, the treatment can comprise surgery or radiotherapy.

The present invention further relates to the COMBINATION OF THE INVENTION for use in the treatment of a proliferative disease, particularly cancer.

The present invention further provides a commercial package comprising as therapeutic agents COMBINATION OF THE INVENTION, together with instructions for simultaneous, separate or sequential administration thereof for use in the delay of progression or treatment of a proliferative disease in a subject in need thereof.

The following Examples illustrate the invention described above; they are not, however, intended to limit the scope of the invention in any way. The beneficial effects of the pharmaceutical combination of the present invention can also be determined by other test models known as such to the person skilled in the pertinent art.

Example 1

Evaluate sensitivity of Compound A and combination efficacy of Compounds A and B in Compound B-sensitive primary human melanoma HMEX1906 xenografts. Since each agent induced tumor stasis or regression in previous studies, goal of current study is to investigate time-to-regrow after treatment with the COMBINATION OF THE INVENTION Tumors are chopped/minced into cell line like suspension (tumors homogenized). 7 mL of matrigel added and 1.5 mL of HBSS. Suspension warmed in palm until Matrigel is thick and implanted with a 18 G needle s.c right flank of female nude mice. Treatment is started 16 days post-implant.

Formulation #1: 0.5% Methyl cellulose
Formulation #2: Compound A in 0.5% Methyl cellulose
Formulation #3: Compound B in 0.5% carboxymethylcellulose + 0.5% Tween80 (CMC + T80)

| Group | Mice | Therapy | Route | Schedule | Dose (mg/kg) | Time Point (hr) post final-dose |
|---|---|---|---|---|---|---|
| 1 | 7 | vehicle | PO | qd | — | — PD |
| 2 | 7 | Compound A | PO | qd | 150 | 4 hrs PD |
| 3 | 7 | Compound A | PO | qd | 250 | 4 hrs PD |

-continued

| 4 | 7 | Compound B | PO | bid | 3 | 4 hrs PD |
| 5 | 7 | Compound A + Compound B | PO | qd/bid | 250 + 3 | 4 hrs PD |

| | Vehicle | Compound A [150 mg/kg] | Compound A [250 mg/kg] | Compound B [3 mg/kg] | Combination A (250 mg/kg) and B (3 mg/kg) |
|---|---|---|---|---|---|
| Anti-tumor activity [day 46] | — | T/C = 7% | 76% reg. | 57% reg. | 91% reg |
| Total complete regressions [day 59] | — | — | 0/7 [0%] | 1/7 [14%] | 5/7 [71%] |
| Median survival [stop dosing day 59] | 39 | — | 78 | 88 | 99 |

Compound A shows significant anti-tumor activity in Braf mutant HMEX1906 xenograft model with stasis T/C=7% at 150 mg/kg,qd and 76% regression at 250 mg/kg,qd dose. Compound B shows 57% regression at 3 mg/kg,bid dose. The COMBINATION OF THE INVENTION shows 91% regression on day 46 of study [31 days of dosing].

Vehicle group and Compound A [150 mg/kg] single agent were dosed for 31 days and terminated after last dose. Compound A [250 mg/kg], Compound B single agent and the COMBINATION OF THE INVENTION were dosed for 45 days and monitored for tumor growth delay after last dose [day 59 of study].

No significant body weight loss in treated animals was observed.

Example 2

Objective:

Evaluate durability of response to Compound A, Compound B and combination of Compounds A and B in primary human melanoma (BRAF mutant) HMEX2613 xenografts. Goal of current study is to investigate time-to-regrow to 500 mm$^3$ after treatment with single agents and with the COMBINATION OF THE INVENTION.

Tumor xenographs are implanted in female nude mice in a manner similar to that described in Example 1. Treatment is started 19 days post-implant and continued for 11 days in the groups dosed with vehicle and Compound A single agent, or 18 days in the groups dosed with Compound B single agent and the COMBINATION OF THE INVENTION.

Formulation #1: 0.5% Methyl cellulose
Formulation #2: Compound A in 0.5% Methyl cellulose
Formulation #3: Compound B in 0.5% carboxymethylcellulose/0.5% Tween80

| Group | # Mice | Compound | Route | Schedule | Dose (mg/kg) |
|---|---|---|---|---|---|
| 1 | 8 | vehicle | PO | qd | — |
| 2 | 8 | Compound B | PO | qd | 20 |
| 3 | 8 | Compound A | PO | qd | 250 |
| 4 | 8 | Compound B + Compound A | PO | qd | 20 + 250 |

Tumor xenografts are implanted in female nude mice in a manner similar to that described in Example 1. Treatment is started 19 days post-implant and continued for 11 days in the groups dosed with vehicle and Compound A single agent, or 18 days in the groups dosed with Compound B single agent and the COMBINATION OF THE INVENTION.

The results are graphically depicted in FIG. 1.

Compound A shows moderate anti-tumor activity in Braf mutant HMEX2613 xenograft model with a T/C of 45%.

Compound B and COMBINATION OF THE INVENTION show complete tumor regression.

Vehicle group and Compound A single agent were dosed for 11 days and then humanely euthanized. Compound B single agent and Compound B/Compound A combination were dosed for 18 days and monitored for tumor regrowth after last dose.

Compound B single agent shows tumor regrowth 5 days post last dose and 37% tumor free animals at the end of the study [5 out of 8 tumors grew back].

COMBINATION OF THE INVENTION shows a growth delay of 26 days post last dose and 62% tumor free animals at the end of the study [3 out of 8 tumors grew back].

No significant body weight lost in treated animals was observed.

Example 3

Objective:

To evaluate the efficacy of COMBINATION OF THE INVENTION in the HMEX1906 primary melanoma model that is grown in the presence of and is resistant to 5 mg/kg Compound B (HMEX1906-R5)

Drug formulation: Compound A is formulated in 0.5% MC/0.5% Tween80 and Compound B is formulated in 20% PEG300/3% ETPGS.

Tumor xenografts are implanted in female nude mice in a manner similar to that described in Example 1. Mice were not dosed with Compound B following tumor chunk implant.

The mice were assigned to the following groups at 18 days post implant with an average tumor volume of 266 mm$^3$ and average body weight of 25 grams.

Groups: 10 mice/group, route PO, dose volume 0.2 mL

Group 1: Vehicle, 0 mg/kg bidx14

Group 2: Compound A, 250 mg/kg qdx21

Group 3: Compound B, 5 mg/kg bidx21

Group 4: Compound A 250 mg/kg qd x21+Compound B 5 mg/kg bid x21

Results:

| Group | Mean change of tumor volume vs control (T/C) (%) | Regression (%) | Mean change of tumor volume (mm3 ± SEM) | Mean change of body weight (% ± SEM) | Survival (Survivors/ Total) |
|---|---|---|---|---|---|
| 1 | 100 | — | 2092 ± 154 | 4.2 ± 2.6 | 7/10* |
| 2 | 4 | — | 86 ± 26 | 5.3 ± 1.4 | 10/10 |
| 3 | 39 | — | 807 ± 106 | 3.5 ± 1.1 | 10/10 |
| 4 | — | 64.32 | −170 ± 45 | 7.1 ± 1.6 | 10/10 |

*3 mice were euthanized due to large tumor

Example 4

Materials and Methods—

Compound stocks are prepared in DMSO at a final concentration of 10 mM. Working stocks are serially diluted in the appropriate cell culture medium in 3-fold increments to achieve final assay concentrations ranging from 2.7 µM to 1.2 nM for Compounds B and D, and 10 µM to 4.6 nM for Compound A.

Cell Lines, Cell Culture, Cell Viability Measurements—

A-375 and WM-266-4 cells were purchased from American Type Culture Collection (ATCC). The A-375 cells were cultured in DMEM medium (ATCC) and the WM-266-4 cells were cultured in EMEM medium (ATCC) both supplemented with 10% fetal bovine serum (Gibco) and incubated at 37° C./5% CO2. The cell lines engineered to express commonly occurring alleles indicative of resistance were acquired from Novartis-Emeryville. These resistant models include, A-375 cells expressing mutant MEK1P124L, truncated p61-BRAFV600E, or mutant NRASQ61K, and WM-266-4 cells expressing mutant MEK1C121S, truncated p61-BRAFV600E, or mutant NRASQ61K. These cells were cultured in the appropriate parental medium with selection marker G418 and in the presence of 5 uM LFE158 (MEK mutants) or LIH720 (truncated p61-BRAFV600E).

Plate Layout, Cell Dispensing and Compound Addition—

For screening, cells were seeded in 80 ul of medium in 384-well plates (Thermo Scientific, cat #4332) at 500 (A-375) or 750 (WM-266-4) cell densities per well using a MultiDrop Combi (Thermo-Fisher) with an 8-channel standard cassette. To promote an even distribution of cells across the entire well, cells were briefly centrifuged at 1000 RPM and incubated at room temperature 30 minutes. All plates were incubated at 37° C., 5% $CO_2$ for 24 h prior to compound addition. Compound stock was freshly prepared in the appropriate culture medium, and added using a PAA robot equipped with a 200 nl pin tool. In a minimum of three replicate wells, single agent and combination effects after 72 hours, were assessed by both quantification of cellular ATP levels via Cell Titer Glo (Promega) according to the manufacturer's protocol and by microscopy imaging. For imaging, cells were fixed to the plates and permeabilized with a solution of 10% PFA, 0.3% TX-100 in PBS via a WellMate dispenser with controlled dispensing speeds. Cell nuclei were stained with Hoechst 33342 (H3570, Invitrogen), and all necessary washing steps were performed by a BioTek washer.

Automated Image Analysis—

Images from the InCell Analyzer 2000 (GE Healthcare, 28-9534-63) were in TIFF format and had a size of 2048× 2048 pixels, capturing the whole well of a 384-well plate. An automated image analysis pipeline was established using custom-made scripts in the open-source, statistical programming language R, and functions of the BioConductor package EBImage. The goal was to quantify the number of viable nuclei (cells) per well as an approximation for cell viability. The pipeline was comprised of seven steps: (I.) smoothing of the image to reduce the number of intensity peaks, (II.) application of a thresholding function to separate the foreground (signal) from the background (noise), (III.) identification of local maxima in the foreground that serve as seeds for the nuclei, (IV.) filtering of local maxima in close proximity, (V.) propagation of the nuclei from remaining local maxima, (VI.) and extraction of object features from the propagated nuclei (numbers of nuclei, size features and intensity features). As a last step (VII.), to exclude debris (e.g. fragmented nuclei) from counting, objects identified in DMSO- and Staurosporin-treated wells were used to obtain feature distributions for viable and fragmented nuclei, respectively. These were used to set cut-offs differentiating between viable and fragmented nuclei. The number of fragmented nuclei was subtracted from the total number of identified objects and the result was reported as final count for that well.

Data Normalization—

Data comprised triplicate measurements for each treatment (compound) condition, 42 replicates of DMSO-treated wells, and duplicates of Staurosporin-treated wells. The data was normalized to the median of the DMSO measurements and summarized by calculating the median of the triplicates. Data was imported into Chalice to calculate compound synergies.

Results:

| Parent Cell LIne | Resistant Allele | Cpd. A IC50 (nM) | Cpd. B IC50 (nM) | Cpd. D IC50 (nM) | Cpd. B + D Lowe Excess Synergy | Cpd. A + B + D Lowe Excess Synergy |
|---|---|---|---|---|---|---|
| | Single Agent IC50 Values and Combination Synergy Scores as determined using ATP-based CTG assay |
| A-375 | — | >10000 | 4 | 51 | 3.0 | 2.7 |
| A-375 | MEK1$^{P124L}$ | >10000 | 333 | >2700 | 7.8 | 1.0 |
| A-375 | p61 BRaf$^{V600E}$ | >10000 | 576 | 961 | 4.6 | 1.0 |
| A-375 | NRAS$^{Q61K}$ | >10000 | 134 | 206 | 4.3 | 2.5 |
| WM-266-4 | — | >10000 | 2 | 50 | 4.2 | 2.7 |
| WM-266-4 | MEK1$^{C121S}$ | >10000 | 35 | 821 | 5.4 | 2.0 |

-continued

| Parent Cell Line | Resistant Allele | Cpd. A IC50 (nM) | Cpd. B IC50 (nM) | Cpd. D IC50 (nM) | Cpd. B + D Lowe Excess Synergy | Cpd. A + B + D Lowe Excess Synergy |
|---|---|---|---|---|---|---|
| WM-266-4 | p61 BRaf$^{V600E}$ | >10000 | 906 | >2700 | 5.8 | 1.6 |
| WM-266-4 | NRAS$^{Q61K}$ | >10000 | 1122 | >2700 | 5.1 | 1.3 |

Single Agent IC50 Values and Combination Synergy Scores as determined using microscopy assay

| | | | | | | |
|---|---|---|---|---|---|---|
| A-375 | — | 3184 | 4 | 57 | 2.4 | 2.7 |
| A-375 | MEK1$^{P124L}$ | >10000 | 300 | >2700 | 9.3 | 1.6 |
| A-375 | p61 BRaf$^{V600E}$ | 8035 | 849 | 969 | 5.9 | 1.7 |
| A-375 | NRAS$^{Q61K}$ | 4208 | 133 | 150 | 4.6 | 4.4 |
| WM-266-4 | — | 630 | 3 | 77 | 4.1 | 3.0 |
| WM-266-4 | MEK1$^{C121S}$ | 806 | 58 | 1210 | 6.3 | 1.5 |
| WM-266-4 | p61 BRaf$^{V600E}$ | 2621 | 933 | >2700 | 6.8 | 0.7 |
| WM-266-4 | NRAS$^{Q61K}$ | 839 | 868 | >2700 | 4.5 | 1.1 |

The invention claimed is:

1. A pharmaceutical combination comprising:
(a) a CDK4/6 inhibitor of the formula

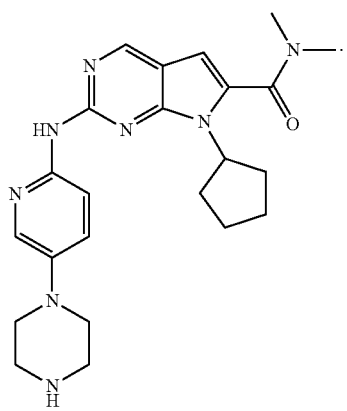 [SMILES: CN(C)C(=O)c1cc2cnc(Nc3ccc(N4CCNCC4)cn3)nc2n1C1CCCC1]

or a pharmaceutically acceptable salt thereof, and
(b) a B-Raf inhibitor of the formula

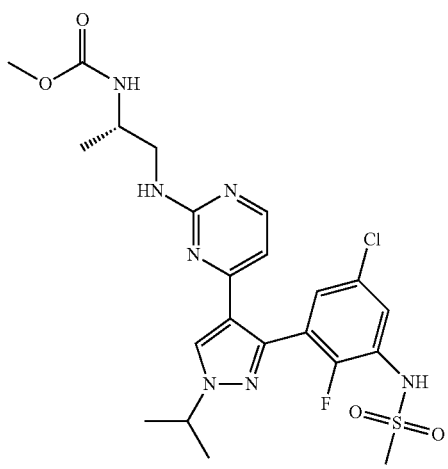 [SMILES: COC(=O)N[C@@H](C)CNc1nccc(-c2cn(C(C)C)nc2-c2cc(Cl)cc(NS(C)(=O)=O)c2F)n1]

or a pharmaceutically acceptable salt thereof,
for simultaneous, separate or sequential administration.

2. The pharmaceutical combination according to claim 1 which further comprises a MEK 1/2 inhibitor.

3. The pharmaceutical combination according to claim 2 wherein the MEK 1/2 inhibitor is a compound of the formula

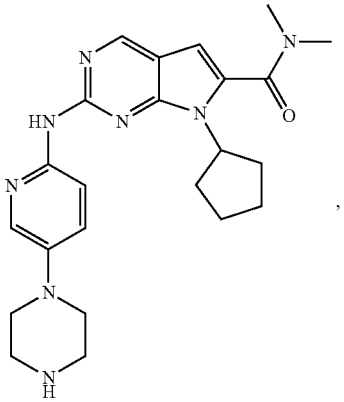 [SMILES: CN(C)C(=O)c1cc2cnc(Nc3ccc(N4CCNCC4)cn3)nc2n1C1CCCC1]

or a pharmaceutically acceptable salt thereof.

4. A method for treating a proliferative disease in a human patient, comprising simultaneously, separately or sequentially administering to the patient a therapeutically effective amount of
(a) a CDK4/6 inhibitor of the formula

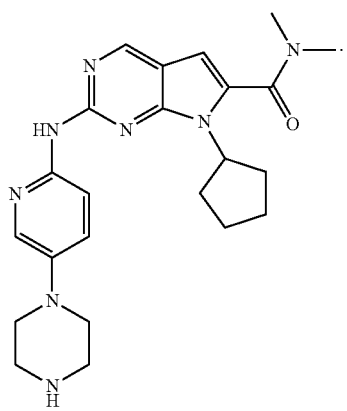 [SMILES: CN(C)C(=O)c1cc2cnc(Nc3ccc(N4CCNCC4)cn3)nc2n1C1CCCC1]

or a pharmaceutically acceptable salt thereof, and (b) a B-Raf inhibitor of the formula

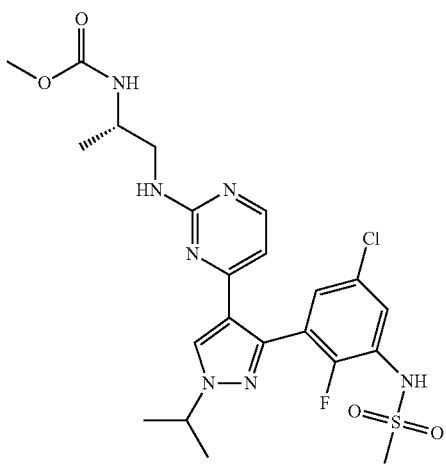 [SMILES: COC(=O)N[C@@H](C)CNc1nccc(-c2cn(C(C)C)nc2-c2cc(Cl)cc(NS(C)(=O)=O)c2F)n1]

or a pharmaceutically acceptable salt thereof.

5. The method according to claim 4, wherein the proliferative disease is melanoma, lung cancer, colorectal cancer (CRC), breast cancer, kidney cancer, renal cell carcinoma (RCC), liver cancer, acute myelogenous leukemia (AML), myelodysplastic syndromes (MDS), non-small-cell lung cancer (NSCLC), thyroid cancer, pancreatic cancer, neurofibromatosis or hepatocellular carcinoma.

6. The method according to claim 5, wherein the proliferative disease is characterized by a B-Raf mutation.

7. The method according to claim 5, wherein the proliferative disease is characterized by a B-Raf V600 mutation.

8. The method according to claim 7, wherein the proliferative disease is melanoma or colorectal cancer.

9. A combined preparation which comprises the pharmaceutical combination according to claim 1.

10. A pharmaceutical composition which comprises the pharmaceutical combination according to claim 1.

11. The method according to claim 7, wherein the B-Raf V600 mutation is a V600E mutation, a V600K mutation, or a V600G mutation.

12. The method according to claim 4, wherein the method further comprises simultaneously, separately or sequentially administering to the patient a therapeutically effective amount of a MEK 1/2 inhibitor.

13. The method according to claim 12, wherein the MEK 1/2 inhibitor is a compound of the formula

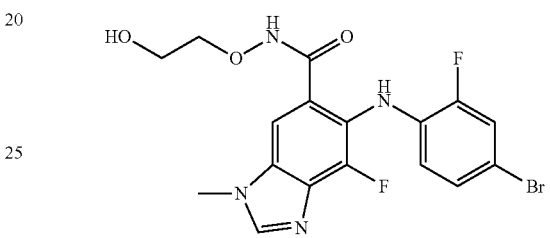

or a pharmaceutically acceptable salt thereof.

* * * * *